(12) United States Patent
Tachizaki

(10) Patent No.: US 6,314,157 B1
(45) Date of Patent: Nov. 6, 2001

(54) ARRANGEMENTS FOR MOUNTING UNITS IN A COMPUTED TOMOGRAPHY SYSTEM

(75) Inventor: Hisashi Tachizaki, Nasu-gun (JP)

(73) Assignee: Kabushiki Kaisha Toshiba (JP)

( * ) Notice: Subject to any disclaimer, the term of this patent is extended or adjusted under 35 U.S.C. 154(b) by 0 days.

(21) Appl. No.: 09/418,507

(22) Filed: Oct. 15, 1999

(30) Foreign Application Priority Data

Oct. 16, 1998 (JP) .................................................. 10-295896

(51) Int. Cl.[7] .................................................. H05G 1/06
(52) U.S. Cl. .................................. 378/4; 378/19; 378/197
(58) Field of Search .................................. 378/4, 19, 193, 378/196, 197, 198

(56) References Cited

U.S. PATENT DOCUMENTS

| | | | |
|---|---|---|---|
| 5,031,198 | * 7/1991 | Deucher et al. | 378/4 |
| 5,703,921 | 12/1997 | Fujita et al. | 378/4 |
| 5,761,269 | 6/1998 | Sugihara et al. | 378/199 |
| 5,784,428 | * 7/1998 | Schmidt | 378/4 |

* cited by examiner

Primary Examiner—Robert H. Kim
Assistant Examiner—Allen C. Ho

(57) ABSTRACT

The rotation component supported rotatably with respect to the gantry includes a cylindrically-shaped rotation base, and a disk-like frame provided in parallel to the bottom surface of the cylinder of the rotation base so as to partition it at substantially a middle way through. The frame has a plurality of unit opening sections for arranging the unit, and further an opening section. The structural elements provided in the rotation component, namely, the X-ray tube unit, signal amplification unit, cooling unit, power units and power control unit are fit into the predetermined unit opening section of the frame, and are fixed onto the inner wall surface of the cylindrical rotation base.

12 Claims, 6 Drawing Sheets

ARRANGEMENTS FOR MOUNTING UNITS IN A COMPUTED TOMOGRAPHY SYSTEM

BACKGROUND OF THE INVENTION

The present invention relates to an X-ray computed tomography apparatus for picking up a tomographic image of an object to be examined, and more specifically to an X-ray computed tomography apparatus having a gantry including a rotation component capable of rotating at high speed.

A rotation component is provided for the gantry of an X-ray computed tomography apparatus (to be called "CT" hereinafter). The rotation component can be rotated continuously by 360° or more with respect to the fixation component of the gantry. Recently, the rotation speed of the rotation component has been increased to such a high speed of 1 sec/rot or higher.

The rotation component has, for example, a disk-like shape, a drum shape, or the like.

The rotation base having the drum shape has a flat ring-shaped rotation base serving as a bottom surface, and a plurality of units such as an X-ray tube unit, X-ray detection unit and cooling unit (these are called "rotation component units") are mounted onto the rotation base via a bracket and fixation bolts.

In the operation for mounting the rotation component units, the operator pulls up the rotation component units and positions the bracket to the unit mount surface of the rotation base. Then, the bracket is fixed to the rotation base with fixation bolts. With this structure, the fixation bolts serve to support not only the weight of the rotation component units, but also the load created by the centrifugal force due to the rotation of the rotation base, which acts on the rotation component units.

In another conventional example of CT, the rotation base is so formed that the cross section thereof has an L-letter shape. The CT of this type is equipped with a frame for mounting units appropriate for the respective rotation component units, and thus rotation component units are mounted on the unit mount frame.

These conventional CTs entail the problems which may be caused by the connection structure between the rotation components and rotation component units, and the structures of the rotation components themselves.

(1) As the rotation component rotates, the load created by the centrifugal force acting on the rotation component unit, is concentrated onto the fixation bolts which fixes the rotation component unit onto the rotation base. For example, in case where the operator fails to tighten fixation bolts for mounting the rotation component unit to the rotation base, it is possible that those bolts which have not tightened come off, and the rotation component unit fly away while the rotation component is rotating. Especially, in the case where the rotation component rotates at high speed, the possibility that the above-described danger occurs is increased, and therefore a sufficient safety cannot be assured for patents or operators.

(2) The position of the center of gravity of each rotation component unit in the rotation axis direction of the rotation component becomes remote from the unit mounting surface of the rotation base. When the rotation component rotates at high speed, the rotation base is deformed such that the opening of the drum is expanded, due to the centrifugal force acting on each rotation component unit. Therefore, it becomes difficult to keep a necessary positioning accuracy of the X-ray transmitting path when the rotation component rotates at high speed. Further, if the rotation base is excessively deformed, it may be even broken, or the deformed base may cause an abnormality in the CT image.

(3) There are occasionally cases where the rotation component unit is removed from the rotation base due to accident or the like. While removing a fixation bolt which connects the rotation component unit to the rotation base, the rotation component unit must be supported from below, or it must be hung from above, or some measures must be taken in order for the rotation component unit to fall. Thus, the operability is very low, and further there can be a problem in terms of safety while removing the unit.

(4) The rotation and lock of the rotation component are performed by a drive mode by which the connection is made with a belt. In case where the belt is broken by damage or any reason, the rotation component cannot longer be locked to stop the rotation. Therefore, there should rise a danger of a possible accident, in which, for example, the operator or the like is accidentally entangled into the rotation component which cannot longer be locked.

There is a tendency that the size of the rotation component unit is increased, and its weight continuously rises. Therefore, an unbalanced section is created in the rotation component as a whole in terms of weight, and there are increasingly a great number of cases where an excessive load is applied at one time on the belt during the maintenance in which rotation component units are replaced. For example, as the maintenance of replacing an X-ray tube unit which has a short life is repeatedly carried out, an excessive load is applied, thus increasing the possibility of the danger that it is broken.

BRIEF SUMMARY OF THE INVENTION

The present invention has been achieved in consideration of the above-described circumstances, and the object thereof is to provide an X-ray computed tomography apparatus having features described below.

(1) An X-ray computed tomography apparatus which is safe from a danger that the rotation component unit will fly away even if the rotation component is rotated, and which has a high rigidity to high-speed rotation.

(2) An X-ray computed tomography apparatus which can prevent a deformation of the rotation component.

(3) An X-ray computed tomography apparatus having a high operability and safety in mounting/removing the rotation component units in the maintenance operation.

(4) An X-ray computed tomography apparatus which can safely lock the rotation component to stop its rotation without applying an excessive load to the belt or which can safely lock the rotation component to stop its rotation even in a structure without the belt.

According to the present invention, there is provided an X-ray computed tomography apparatus comprising: a gantry; a stationary component set in the gantry; and a rotation component supported rotatably with respect to the stationary component in the gantry, the rotation component comprising: a rotation base having a cylindrical shape; a disk-like frame having an opening portion for arranging a unit, and set in parallel to a bottom surface of the cylinder of the rotation base so as to partition it at substantially a middle of the cylinder, the unit being fit into the opening portion and fixed to an inner wall surface of the rotation base.

According to the present invention, there is provided another X-ray computed tomography apparatus comprising:

a gantry; a stationary component set in the gantry; and a rotation component supported rotatably with respect to the stationary component in the gantry, the rotation component comprising: a rotation base having a cylindrical shape; and a disk-like frame having an opening portion for arranging a unit, and set in parallel to a bottom surface of the cylinder of the rotation base, the unit being fit into the opening portion and fixed to an inner wall surface of the rotation base, and wherein a position of the center of the gravity of the unit substantially coincides to a position of a plane of the disk-like frame.

According to the present invention, there is provided still another X-ray computed tomography apparatus comprising: a gantry; a stationary component set in the gantry; and a rotation component supported rotatably with respect to the stationary component in the gantry, the rotation component comprising: a rotation base having a cylindrical shape; a guide rail arranged on an inner surface wall of the rotation base; and a unit mounted to the rotation base as being slid along the guide rail.

According to the present invention, there is provided still another X-ray computed tomography apparatus comprising: a gantry; a stationary component set in the gantry; a rotation component supported rotatably with respect to the stationary component in the gantry, the rotation component comprising: a rotation base having a cylindrical shape and a fixation hole in its circumferential surface; and a unit fit mounted to the rotation base; and a lock mechanism, set in the stationary component, including a rod-like component which can be inserted to the fixation hole, so as to lock the rotation component to stop from rotating.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION

Embodiments of the present invention will now be described with reference accompanying drawings.

Figure 1:
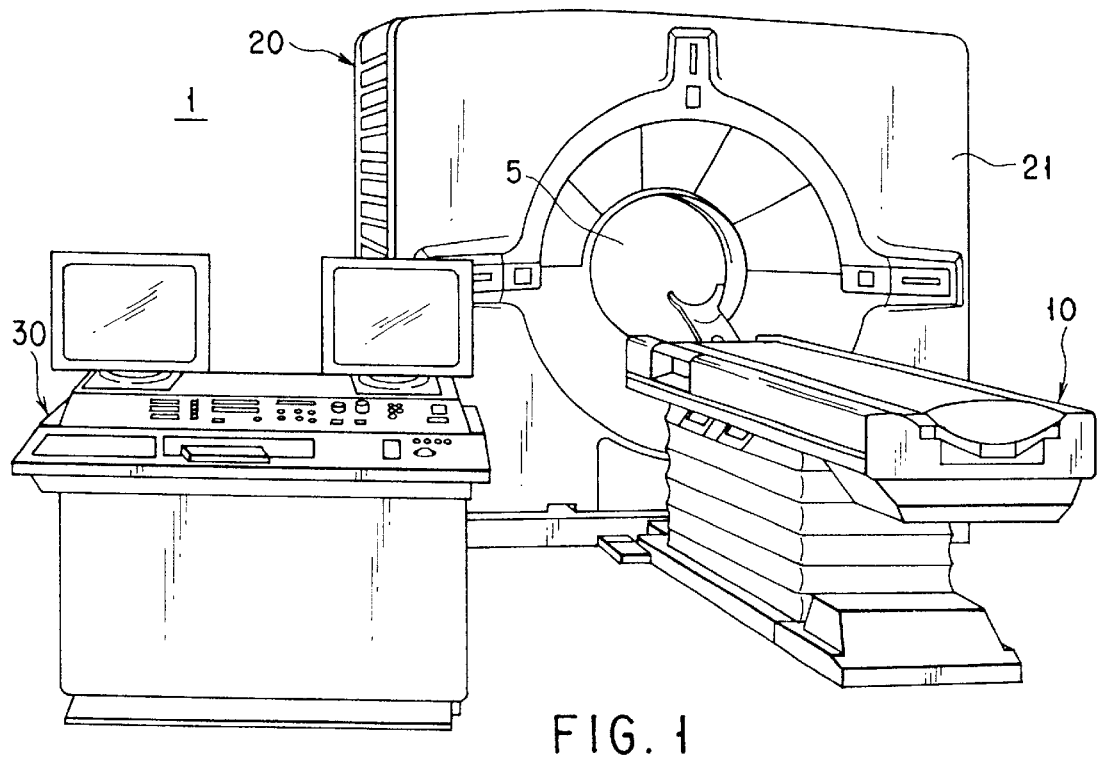
FIG. 1 is a diagram showing a perspective view of a CT according to the first embodiment of the present invention.
Figure 2:
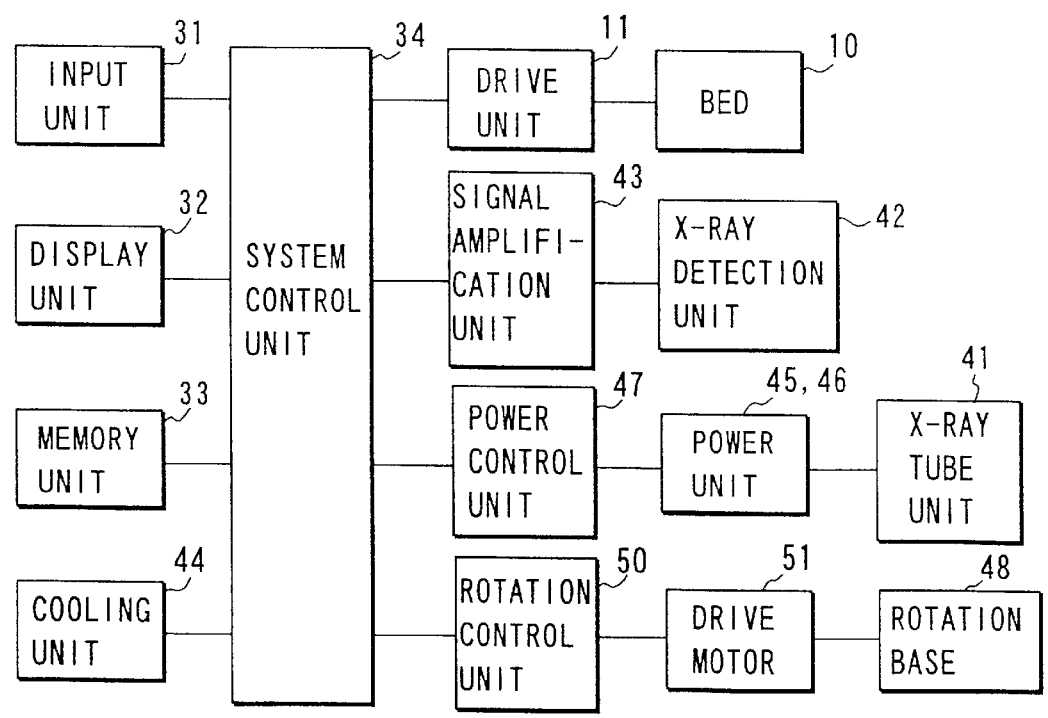
FIG. 2 is a block diagram showing the unit structure of the CT according to the first embodiment.

FIG. 1 is a perspective view of the CT according to the first embodiment of the present invention, and FIG. 2 is a block diagram showing the unit structure of the CT according to this embodiment.

As shown in FIG. 1, a CT 1 mainly consists of a bed 10, a gantry 20 and a control device 30. The bed 10 is equipped with a drive unit 11 for conveying an object to be examined (for example, patient) (not shown), which is placed thereon, to an opening section 5 formed in the gantry 20. The internal structure of the gantry 20 is covered by a gantry cover 21, and the gantry has a mechanism of irradiating X-rays from the surrounding of the object inserted to the opening portion 5, and detecting those X-rays which have transmitted through the object.

As shown in FIG. 2, the CT 1 includes a drive unit 11, an input unit 31, a display unit 32, a memory unit 33, an X-ray tube unit 41, power units 45 and 46, a power control unit 47, an X-ray detection unit 42, a signal amplification unit 43, a cooling unit 44, a rotation base 48, a drive motor 51 and a rotation control unit 50.

The control device 30 shown in FIG. 1 serves to control the entire operation of the CT1 of this embodiment, and it consists of the input unit 31, display unit 32, memory unit 33 and system control unit 34.

The input unit 31 is a unit to which various commands such as scan instruction for an X-ray CT image, and various parameters necessary for imaging, are inputted. The display unit 32 is designed to display the above-mentioned parameters and the X-ray CT image which has been scanned. The memory unit 33 is designed to store the parameters and the X-ray CT image which has been scanned. The system control unit 34 is designed to control the operation of the units of the CT1.

Figure 3A:
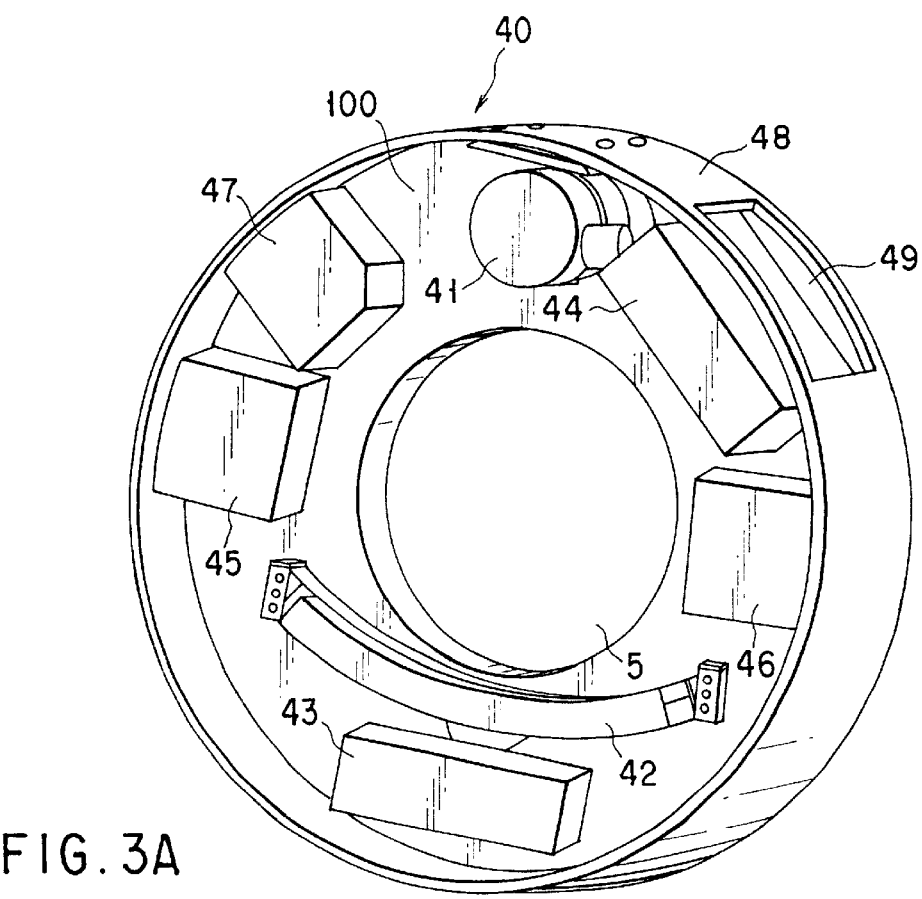
FIG. 3A is a perspective view showing the structure of the rotation component according to the first embodiment.
Figure 3B:
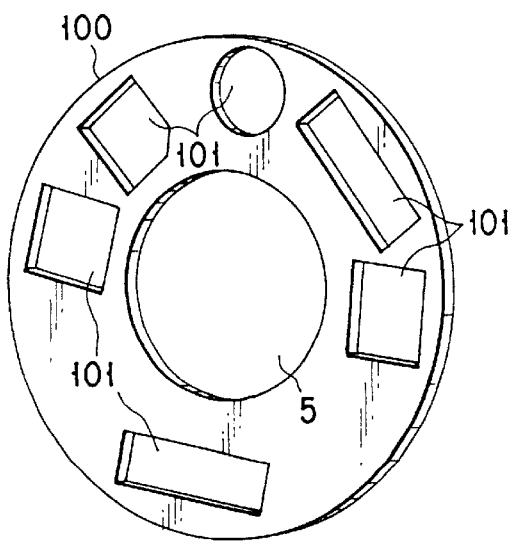
FIG. 3B is a perspective view showing the structure of the frame according to the first embodiment.

FIGS. 3A and 3B are perspective views showing the structure of the rotation section of the CD of this embodiment.

The rotation section 40 shown in FIG. 3A is provided inside the gantry 20, and has a rotation base 48 having a cylindrical shape, and a disk-like frame 100 provided in parallel to the bottom surface of the cylinder of the rotation base 48 so as to partition it at substantially a middle way through. As can be seen in FIG. 3B, the frame 100 has a plurality of unit opening sections 101 for arranging the unit, and has an opening portion 5. The rotation base 48 has a heat radiating opening 49 formed therein for radiating heat generated in each unit to the outside.

In the rotation component 40, a plurality of rotation component units are arranged at predetermined respective positions. In more detail, the X-ray tube unit 41 for generating X-rays, the X-ray detection unit 42 provided at a position to oppose the tube unit 42 via an object, for detecting X-rays having transmitted the object after being radiated from the X-ray tube unit 41, the signal amplification unit for amplifying a signal detected by the X-ray detection unit, the cooling unit provided adjacent to the X-ray tube unit 41, for cooling the X-ray tube unit 41, the power units 45 and 46 for supplying tube voltages (tube currents) to the X-ray tube unit 41, and the power control unit 47 for controlling the power units 45 and 46, are provided.

To the cylindrical rotation base 48, the rotational force of the drive motor 51 is given via a belt or the like, as it is controlled by the rotation control unit 50. The entire rotation unit 40 rotates around the axis of the object inserted to the opening section 5 as a central axis. The rotation speed of the rotation component 40 is, for example, 1 [sec/rotation] or more, especially 0.5 [sec/rotation] or more. That is, the time necessary for the rotation component 40 to rotate around the object just for once in order to obtain an X-ray CT image of the object is 1 second or less, especially 0.5 seconds or less.

While the rotation component 40 rotates around the object once, the rotation component units operate in the following steps. That is, as being controlled by the power control unit 47, predetermined tube voltages (tube currents) are supplied to the X-ray tube unit 41 from the power units 45 and 46, and thus X-rays are radiated from the X-ray tube unit 41. The X-rays are applied onto the object, and the transmitting X-rays are detected by the X-ray detection unit 42.

The detection signal for the X-rays detected by the X-ray detection unit 42 is amplified by the signal amplification unit 43, and then supplied to the system control unit 34. The system control unit 34 carries out a preset image reconstruction process on the basis of the detection signal, and thus at least one X-ray CT image is created. The X-ray CT image is displayed on the display unit 32.

Here, the structure of mounting the rotation component unit to the rotation component, according to this embodiment, will now be described.

As illustrated in FIG. 3A, the rotation component 40 has the rotation base 48 having a cylindrical shape, and a disk-like frame 100 provided in parallel to the bottom surface of the cylinder of the rotation base 48 so as to partition it at substantially a middle way through. The frame 100 has a plurality of unit opening portions 101 for arranging the unit as shown in FIG. 3B.

The X-ray tube unit 41, signal amplification unit 43, cooling unit 44, power units 45 and 46, and power control unit 47, which are the structural materials provided in the rotation component 40, are fit into a predetermined unit opening portion 101 of the frame 100, and are fixed onto the inner wall surface of the cylindrical rotation base 48.

Figure 4:
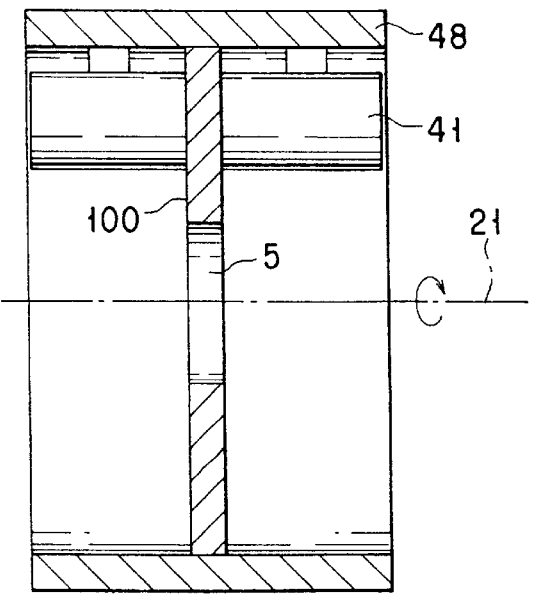
FIG. 4 is a cross sectional view of the rotation component according to the first embodiment.

For example, as shown in FIG. 4, the X-ray tube unit 41 is fit into the unit opening portion 101, and therefore the section of the center of gravity of the X-ray tube unit 41 is supported by the frame 100. Further, the X-ray tube unit 41 is fixed with fixation bolts by two sections of the inner wall surface of the rotation base 48. Here, the number of fixation points is not limited to two of the above case.

In the case where the rotation portion 40 is rotated around the rotation axis 21 as a central axis, the X-ray tube unit 41 also rotates around the rotation axis 21 as the central axis. At this point, a centrifugal force in the direction away from the rotational axis 21 (outward direction) acts on the X-ray tube unit 41.

However, even if the X-ray tube unit 41 is swung radially outwards to be flown away due to the centrifugal force, it is pressed against the wall surface of the inner side of the rotation base 48, and therefore the X-ray tube unit 41 would not fly away.

Therefore, even in case where the operator fails to tighten fixation bolts during the operation of mounting the X-ray tube unit 41 onto the rotation base 48, and fixation bolts come off while the rotation component 40 is rotating at high speed, the rotation component units including the X-ray tube unit 41 are prevented from flying away due to the centrifugal force. Thus, the safety for patients and operators can be improved.

The disk-like frame 100 is provided in parallel to the bottom surface of the cylinder of the rotation base 48 so as to partition it at substantially a middle way through, and the position of substantially the center of gravity of each of the units including the X-ray tube unit 41 is supported by the frame 100. With this characteristic structure, the rigidity of the rotation component 40 becomes extremely high. Consequently, the deformation of the rotation base 48 can be prevented even in the case where a force created by reason that the centrifugal force due to the rotation of the rotation base 48 acts on the rotation component units, acts on the rotation base 48.

Therefore, a necessary positioning accuracy for the X-ray transmission path at high speed rotation can be surely achieved, and therefore it becomes possible to prevent an abnormality of a CT image in advance.

Next, the second embodiment of the present invention will now be described.

The second embodiment is a CT equipped with a mechanism for mounting rotation component units by means of guide rail. The appearance and unit structure of the CT are the same as those of the first embodiment described above.

Figure 5:
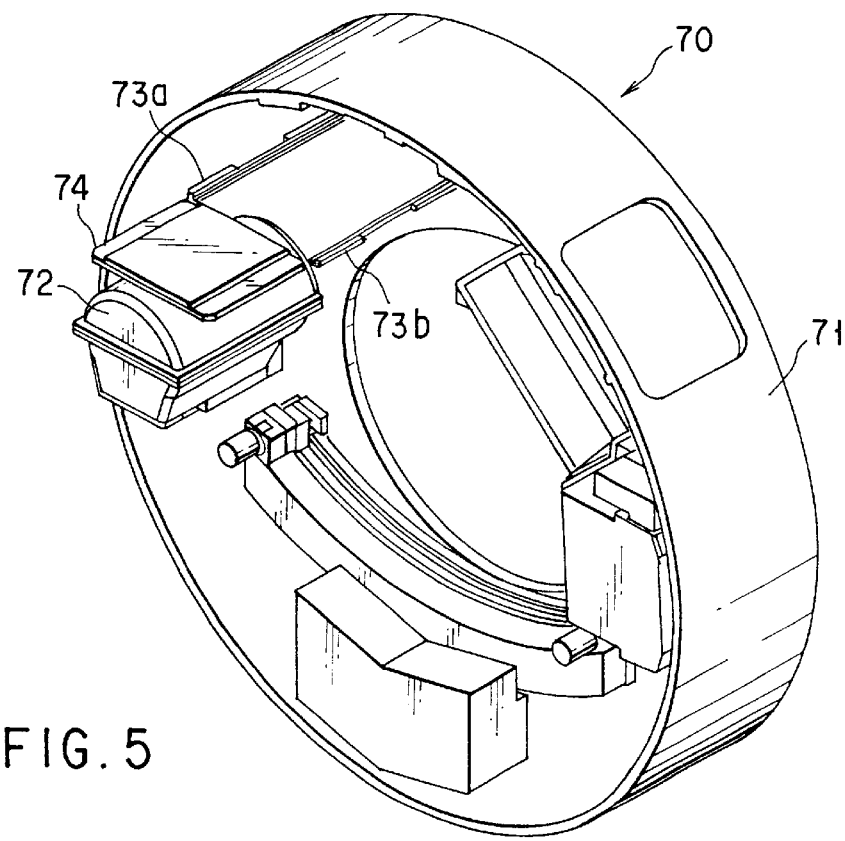
FIG. 5 is a perspective view showing the structure of the rotation component of a CT according to the second embodiment.
Figure 6:
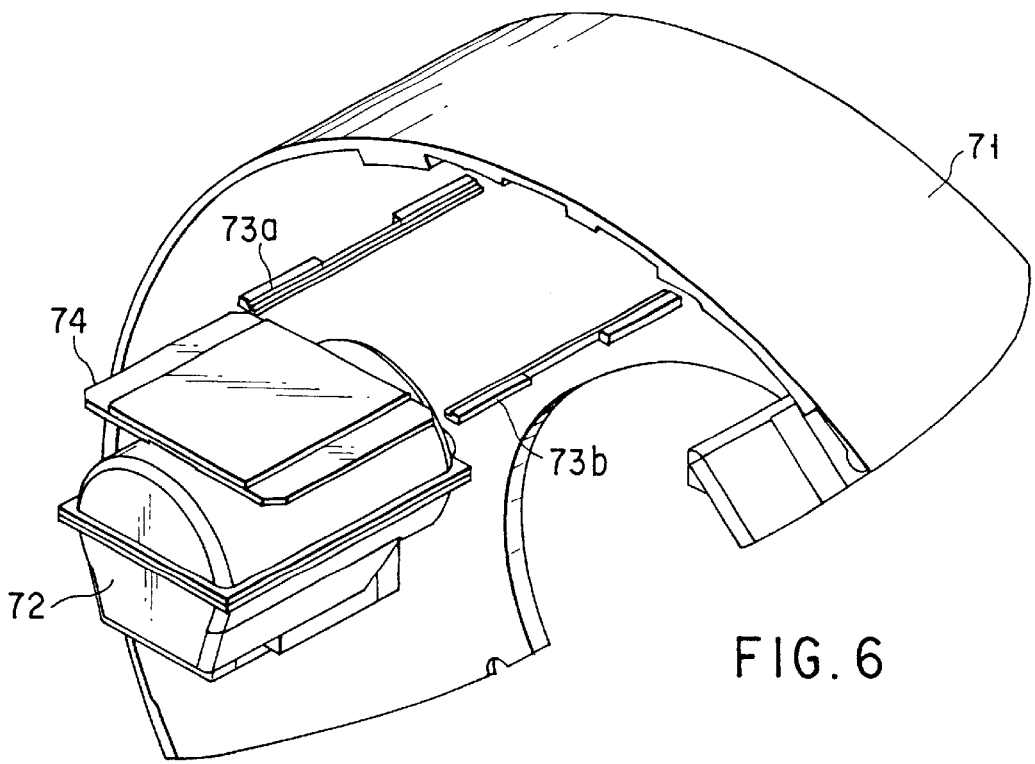
FIG. 6 is a perspective view showing the structure of mounting the unit to the rotation base according to the second embodiment.

FIG. 5 is a perspective view showing the rotation component of the CT according to the second embodiment of the present invention.

As in the first embodiment, the rotation component of this embodiment has a rotation base 71 having a cylindrical shape. FIG. 5 illustrates a partially exploded view of the rotation base 71. On the inner wall surface of the rotation base 71, two guide rails 73a and 73b are arranged.

In the X-ray tube unit 72 as an example of the rotation component unit mounted on the rotation base 71, a guide component 74 is provided on the mount surface side of the rotation base 71. The guide component 74 is engaged with the guide rails 73a and 73b of the rotation base 71 by the operator, and the X-ray tube unit 72 is slid along the rotation axis direction (the rotation axis 21 illustrated in FIG. 1) of the rotation component.

Figure 7A:
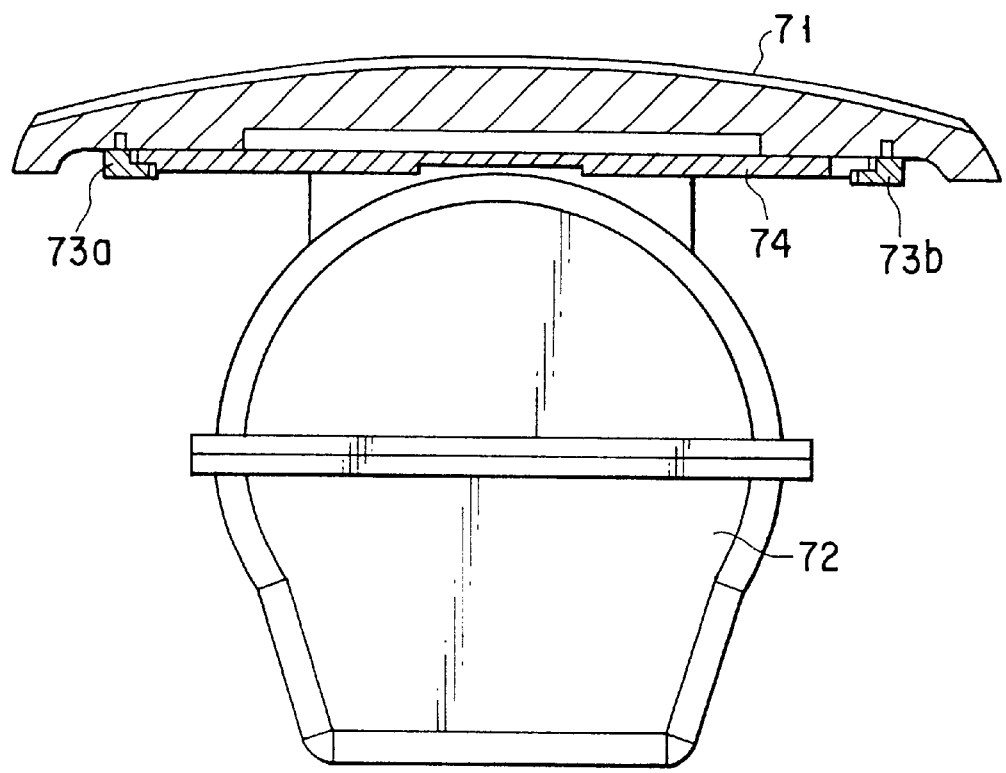
FIG. 7A is a cross sectional view showing the structure of mounting the unit to the rotation base according to the second embodiment.

As shown in the cross sectional view of FIG. 7A, the cross section of each of the guide rails 73a and 73b has an L-letter shape, whereas the cross sections of both ends of the guide component 74 have an upside-down L-letter shape. With such structures, the guide rail 73a and one end of the guide component 74 are engaged with each other, and the guide rail 73b and the other end of the guide component 74 are engaged with each other. Thus, the X-ray tube unit 72 is slidably supported by both of the guide rails 73a and 73b via the guide component 74.

Therefore, even in the case where the X-ray tube unit 72 is mounted when the rotational position of the rotation base 71 portion shown in FIG. 5 is staying at an above position, a possible accident that the unit falls vertically downwards (that is, downwards on document sheet) can be prevented before happening.

With the slide mechanism described above, the X-ray tube unit 72 mounted to the rotation base 71 may be tightly fixed to the rotation base 71 with fixation bolts.

Figure 7B:
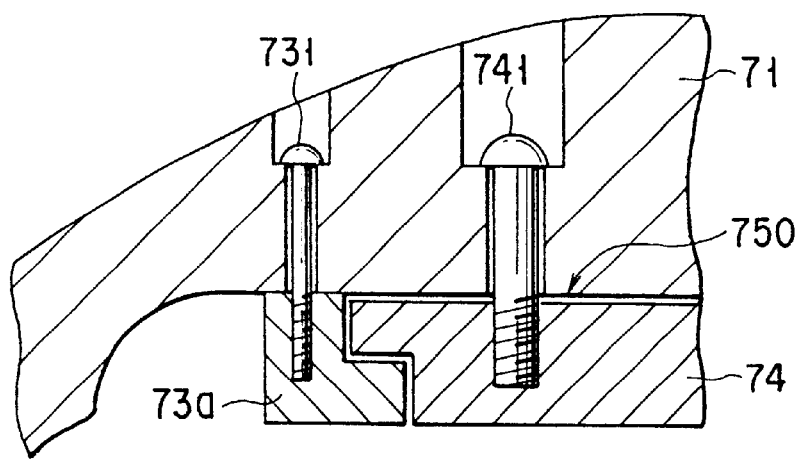
FIG. 7B is a cross sectional view showing the structure of mounting the unit to the rotation base according to the second embodiment in more detail.

FIG. 7B is a cross sectional view illustrating in detail an embodiment in which the X-ray tube unit 72 is fixed to the rotation base 71 with fixation bolts.

First, the guide rail 73a is fixed with respect to the rotation base 71 by a fixation bolt 731 pinned from the outer side of the rotation base 71.

Next, the guide component 74 is fixed with respect to the rotation base 71 by a fixation bolt 741 similarly pinned from the outer side of the rotation base 71.

As is clear from this figure, a flat portion (surface area) 750 is formed in the rotation base 71, forces (centrifugal forces, here) acting from the guide component 74 and the X-ray tube unit 72 are received by the flat portion 750.

The direction of pinning the fixation bolts 731 and 741 may be from the inner side of the rotation base 71. In this case, a thread groove is formed not on the side of the guide rail 73a and the guide component 74, but on the rotation base side 71.

According to the second embodiment described above, it becomes possible to easily mount a rotation component unit (namely, X-ray tube unit 72) via a slide mount mechanism, and therefore the operability and safety in, for example, the maintenance operation for replacing the rotation component unit, are improved. Further, even if the centrifugal force is created due to the high-speed rotation of the rotation component, the rotation component unit is pressed against the inner wall of the rotation base, and therefore an excessive load which is more than the weight of the rotation component unit of itself is not applied to the guide rail. As a result, such an accident that the rotation component unit falls off due to a damage created to the guide rail, can be prevented before happening.

It should be noted that the second embodiment and first embodiment can be combined together. More specifically, there is an alternative structure in which the disk-like frame 100 of the first embodiment is provided in parallel to the bottom surface of the cylinder of the rotation base 71 so as to partition it at substantially a middle way through, and as the structural materials provided in the rotation component 40, the X-ray tube unit 41, signal amplification unit 43, cooling unit 44, power units 45 and 46 and power control unit 47, which are described in the first embodiment, are fit into the preset unit opening portion 101 of the frame 100 by a slide via the guide rail.

Next, the third embodiment of the present invention will now be described.

The third embodiment is a CT equipped with a lock mechanism for the rotation component, which is useful for the maintenance operation including the rotation component unit is removed from the rotation base due to a trouble.

Figure 8:
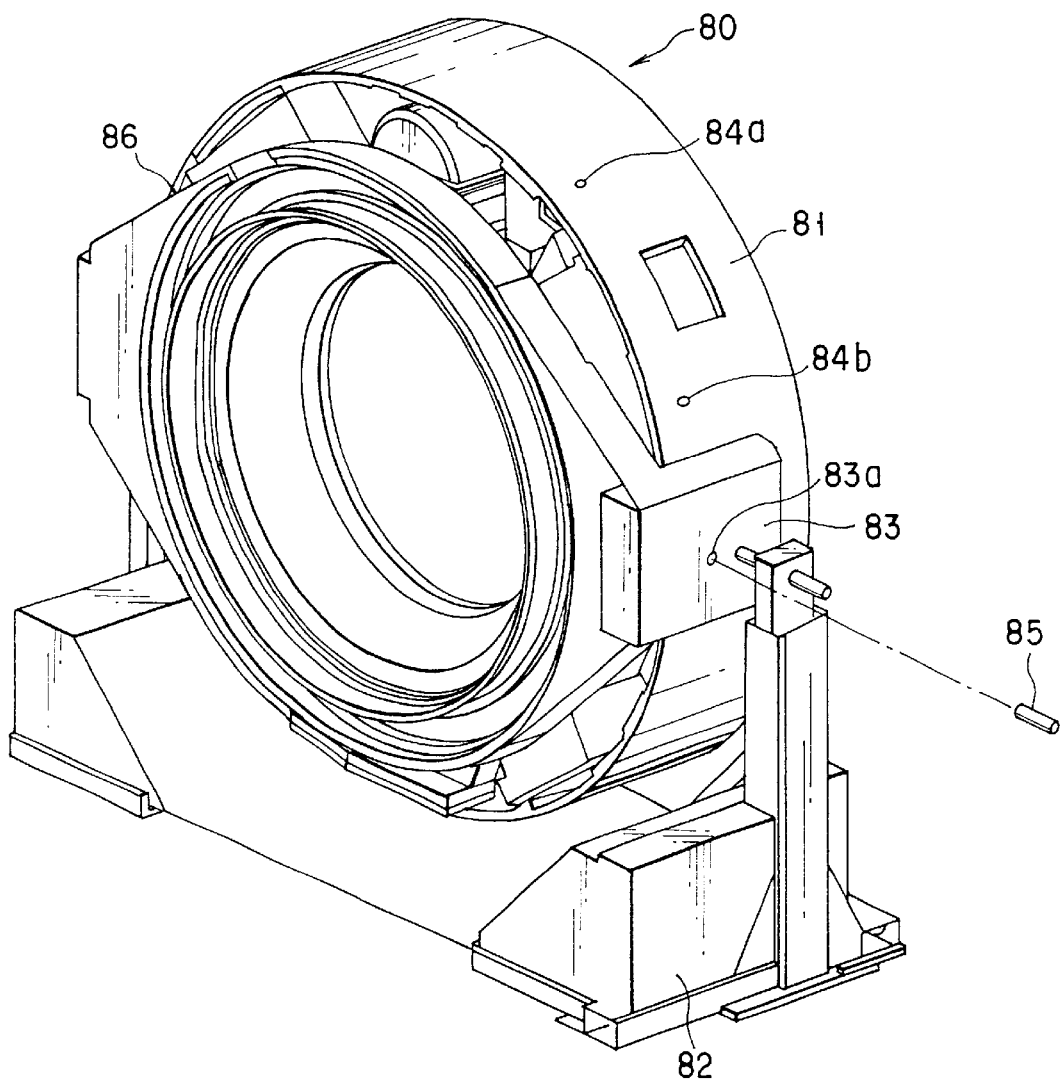
FIG. 8 is a perspective view, taken from back, showing the rotation component according to the third embodiment and a stand for rotatably supporting the rotation component.

FIG. 8 is a rear perspective view illustrating the rotation component of the CT according to the third embodiment of the present invention, and a stand for rotatably supporting the rotation component.

As can be seen in this figure, the cylindrically shaped rotation base 81, which is s structural element of the rotation component 80, is rotatably supported by arm portions 83 and 86 of the stand 82. To the rotation base 81, a plurality of rotation component units are mounted by a mount mechanism similar to that of the first or second embodiment, or some other mechanism different from these.

Fixation holes 84a and 84b are made in the outer circumferential surface of the rotation base 81. These fixation holes 84a and 84b each have such a diameter and depth that a rod-like pin component 85 can be inserted thereto, and the positions of the arrangement of the holes are determined in accordance with the rotation component unit provided on the inner circumferential surface of the base.

In the arm portion 83, a pin insertion hole 83a to which the pin component 85 is inserted is formed. It should be noted that the pin insertion hole 83a may be formed at an appropriate section other than the arm portion 83. For example, it may be formed at a section which is easily accessible by the operator via the gantry cover 21 (especially, side cover). Further, it is only natural that the pin insertion hole must be formed in an immobile portion not in a rotation section.

For example, in order to replace a rotation component unit in the replacement maintenance due to a trouble or like, the rotation component unit is moved by rotation so that the operation becomes more easily for the operator. Let us suppose here that the fixation hole in the rotation base 81, which corresponds to the rotation component unit, is that denoted by reference numeral 84b.

In the case where the structure of the second embodiment is applied, when the rotation component unit is moved by rotation to a section near the arm portion 83 or 86, it becomes more easy to withdraw the rotation component unit along the guide rails 73a and 73b. Here, the guide rails 73a and 73b are arranged at the following positions. That is, the rail 73a is situated at an upper side in the vertical direction, and the rail 73b is situated at a lower side.

When the rotation component unit is moved by rotation to a section near the arm portion 83 or 86, the fixation hole 84b in the rotation base 81, which corresponds to the rotation component unit, is situated just at a section close to the pin insertion hole 83a.

In this state, the operator inserts the pin component 85 to the fixation hole 84b from the pin insertion hole 83a. In this manner, the rotation base 81 is locked so that it will not rotate. The pin component 85 is made of a metal or other mater, which as a mechanical strength sufficient to stop the rotation of the rotation component 80.

An alternative version of the third embodiment is characterized by the automatic positioning for the fixation holes, which is carried out after the detection of the positions of the holes, and the automatic insertion (that is, the automatic lock) of the pin component 85, which is carried out by the pin insertion unit.

Figure 9:
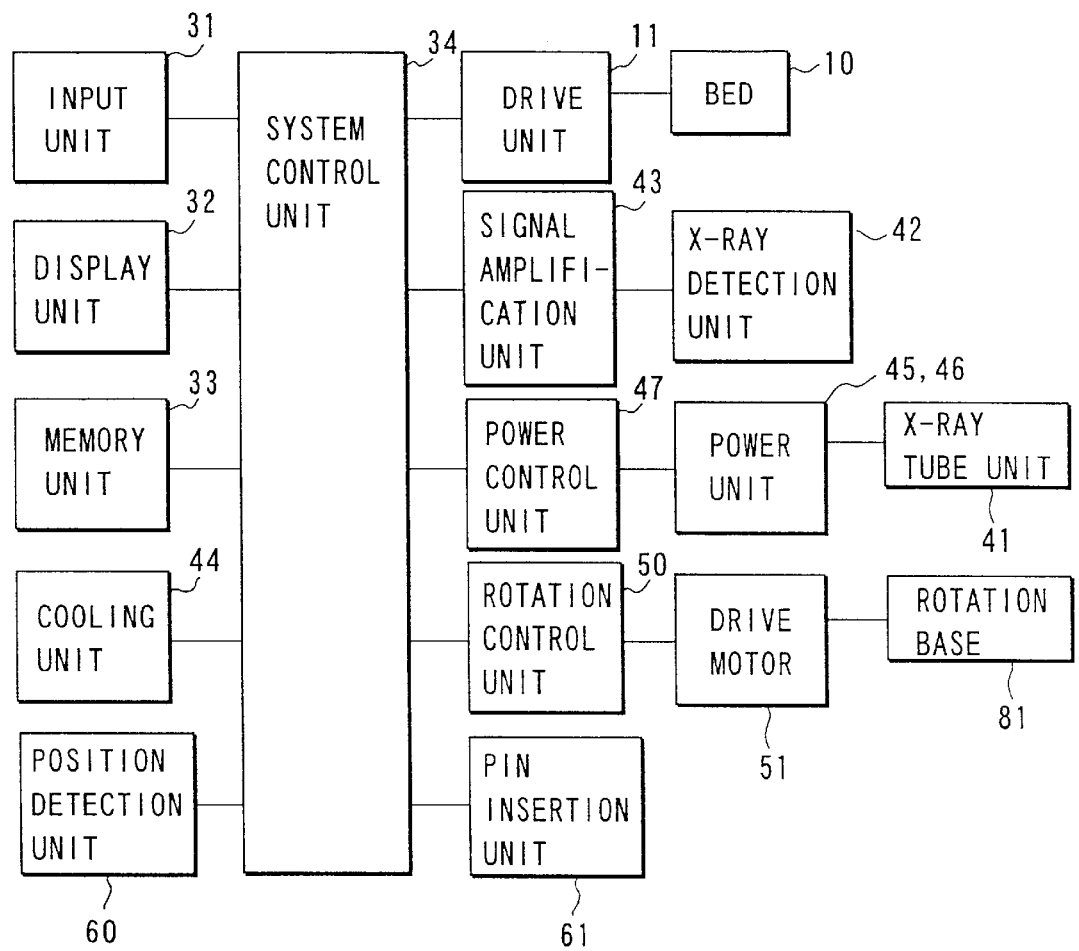
FIG. 9 is a block diagram showing the unit structure of the CT according to the third embodiment.

FIG. 9 is a block diagram showing the unit structure of the CT according to this embodiment. The unit structure of the CT of this embodiment is made on the basis of that of the first embodiment shown in FIG. 2, with addition of a position detection unit 60 and a pin insertion unit 61. The position detection unit 60 has a position encoder for detecting the rotational position of the rotation base 81.

The position detection unit 60 detects the position of the rotation component 80 set by a rotational movement, which is now in a still state, is detected by the position encoder. The system control unit 34 calculates the relationship between the position of the fixation hole 84a (or 84b) and that of the pin insertion hole 83a in the arm portion 83 on the basis of the result of the detection by the position detection unit 60.

On the basis of the result of the calculation, the system control unit 45 controls the rotation control unit 50, and drives the rotation base 81 to rotate, via a belt by means of the drive motor 51, and thus the position of the pin insertion hole 83a is made to coincide with the position of the fixation hole 84a (or 84b).

According to the third embodiment described above, the CT has a mechanism for locking the rotation component 80 to stop with the pin component 85 having a mechanical strength sufficient to stop the rotation of the rotation component 80, and therefore the load applied to the belt which mechanistically connects the rotation portion and drive motor with each other, when locking the component can be markedly decreased. Especially, even in the case where an unbalance in terms of weight is temporarily created in the rotation component during the maintenance operation of the replacement of the rotation component unit, an excessive load is not applied onto the belt, thereby preventing the damage or breakage of the belt. Consequently, the reliability of the locking operation of the rotation component can be improved, and therefore a possible accident in which the operator is entangled into the rotation component due to the breakage of the belt can be prevented, thus improving the safety.

As described above, according to the present invention, there is provided an X-ray computed tomography apparatus having features described below.

(1) An X-ray computed tomography apparatus which is safe from a danger that the rotation component unit will fly away even if the rotation component is rotated, and which has a high rigidity to high-speed rotation.

(2) An X-ray computed tomography apparatus which can prevent a deformation of the rotation component.

(3) An X-ray computed tomography apparatus having a high operability and safety in mounting/removing the rotation component units in the maintenance operation.

(4) An X-ray computed tomography apparatus which can safely lock the rotation component to stop its rotation without applying an excessive load to the belt or which can safely lock the rotation component to stop its rotation even in a structure without the belt.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An X-ray computed tomography apparatus comprising:
   a gantry;
   a stationary component set in the gantry; and
   a rotation component supported rotatably with respect to the stationary component in the gantry, the rotation component comprising:
      a rotation base having a cylindrical shape;
      a disk-like frame having an opening portion for arranging a unit, and set in parallel to a bottom surface of the cylinder of the rotation base so as to partition it at substantially a middle of the cylinder, the unit being fit into the opening portion and fixed to an inner wall surface of the rotation base.

2. The X-ray computed tomography apparatus according to claim 1, wherein a position of the center of the gravity of said unit substantially coincides to a position of a plane of said disk-like frame.

3. The X-ray computed tomography apparatus according to claim 1, wherein a rotation speed of said rotation component is 1 or more.

4. The X-ray computed tomography apparatus according to claim 1, wherein a surface area for receiving a force acting from said unit is formed on said rotation base.

5. An X-ray computed tomography apparatus comprising:
   a gantry;
   a stationary component set in the gantry; and
   a rotation component supported rotatably with respect to the stationary component in the gantry, the rotation component comprising:
      a rotation base having a cylindrical shape; and
      a disk-like frame having an opening portion for arranging a unit, and set in parallel to a bottom surface of the cylinder of the rotation base, the unit being fit into the opening portion and fixed to an inner wall surface of the rotation base, and
   wherein a position of the center of the gravity of the unit substantially coincides to a position of a plane of the disk-like frame.

6. An X-ray computed tomography apparatus comprising:
   a gantry;
   a stationary component set in the gantry; and
   a rotation component supported rotatably with respect to the stationary component in the gantry, the rotation component comprising:
      a rotation base having a cylindrical shape;
      a guide rail arranged on an inner surface wall of said rotation base; and
      a unit mounted to said rotation base as being slid along said guide rail.

7. The X-ray computed tomography apparatus according to claim 6, wherein a rotation speed of said rotation component is 1 or more.

8. The X-ray computed tomography apparatus according to claim 6, wherein a surface area for receiving a force acting from said unit is formed on said rotation base.

9. An X-ray computed tomography apparatus comprising:
   a gantry;
   a stationary component set in the gantry;
   a rotation component supported rotatably with respect to the stationary component in the gantry, the rotation component comprising:
      a rotation base having a cylindrical shape and a fixation hole in its circumferential surface; and
      a unit fit mounted to said rotation base; and
   a lock mechanism, set in the stationary component, including a rod-like component which can be inserted to said fixation hole, so as to lock said rotation component to stop from rotating.

10. The X-ray computed tomography apparatus according to claim 9, wherein a rotation speed of said rotation component is 1 or more.

11. The X-ray computed tomography apparatus according to claim 9, wherein said lock mechanism includes an insertion hole, and said rod-like component is inserted to said fixation hole of said rotation base via the insertion hole.

12. The X-ray computed tomography apparatus according to claim 9, wherein said lock mechanism is formed on an arm component of said stationary component in said gantry.

* * * * *

UNITED STATES PATENT AND TRADEMARK OFFICE
CERTIFICATE OF CORRECTION

PATENT NO. : 6,314,157 B1
DATED : November 6, 2001
INVENTOR(S) : Tachizaki

It is certified that error appears in the above-identified patent and that said Letters Patent is hereby corrected as shown below:

<u>Title page,</u>
Item [73], the Assignee information should read:
-- [73] Assignee: Kabushiki Kaisha Toshiba,
Kawasaki (JP) --

Signed and Sealed this

Twelfth Day of March, 2002

Attest:

Attesting Officer

JAMES E. ROGAN
*Director of the United States Patent and Trademark Office*